United States Patent
Levecq et al.

(10) Patent No.: US 9,507,134 B2
(45) Date of Patent: Nov. 29, 2016

(54) METHOD AND OPTICAL DEVICE FOR SUPER-RESOLUTION LOCALIZATION OF A PARTICLE

(75) Inventors: Xavier Levecq, Gif sur Yvette (FR); Jordi Andilla, Barcelona (ES)

(73) Assignee: IMAGINE OPTIC, Orsay (FR)

( * ) Notice: Subject to any disclaimer, the term of this patent is extended or adjusted under 35 U.S.C. 154(b) by 0 days.

(21) Appl. No.: 14/234,038

(22) PCT Filed: Jul. 10, 2012

(86) PCT No.: PCT/EP2012/063511
§ 371 (c)(1),
(2), (4) Date: Apr. 24, 2014

(87) PCT Pub. No.: WO2013/010859
PCT Pub. Date: Jan. 24, 2013

(65) Prior Publication Data
US 2015/0042778 A1 Feb. 12, 2015

(30) Foreign Application Priority Data

Jul. 21, 2011 (FR) ...................................... 11 56647

(51) Int. Cl.
| | | |
|---|---|---|
| G02B 27/58 | (2006.01) | |
| G02B 21/00 | (2006.01) | |
| G02B 26/06 | (2006.01) | |
| G02B 23/26 | (2006.01) | |

(52) U.S. Cl.
CPC ........... *G02B 21/0004* (2013.01); *G02B 26/06* (2013.01); *G02B 27/58* (2013.01)

(58) Field of Classification Search
CPC ... G02B 27/58; G02B 23/26; G02B 27/0025
See application file for complete search history.

(56) References Cited

U.S. PATENT DOCUMENTS

| | | | | |
|---|---|---|---|---|
| 2003/0007124 A1* | 1/2003 | Levine | ................... | A61F 9/008 351/206 |
| 2005/0207003 A1 | 9/2005 | Kobayashi | | |
| 2007/0216867 A1* | 9/2007 | Campbell | ........... | A61F 9/00806 351/246 |

(Continued)

OTHER PUBLICATIONS

Harris et al., "Single-Molecule DNA Sequencing of a Viral Genome," Science vol. 320, 106 (2008) (4 pages).

(Continued)

*Primary Examiner* — Andy Rao
*Assistant Examiner* — Obafemi Sosanya
(74) *Attorney, Agent, or Firm* — Osha Liang LLP

(57) ABSTRACT

A super-resolution microscopy method includes forming an image of an emitting particle in a detection plane of a detector by a microscopy imaging system and correcting, by a wavefront-modulating device, at least some of the optical defects present between the emitting particle and the detection plane. The method further includes introducing, via the wavefront-modulating device, a deformation of the wavefront emitted by the emitting particle, of variable amplitude, allowing a bijective relationship to be formed between the shape of the image of the emitting particle in the detection plane and the axial position of the emitting particle relative to an object plane that is optically conjugated with the detection plane by the microscopy imaging system. The method further includes controlling the amplitude of the deformation of the wavefront by controlling the wavefront-modulating device, as a function of the given range of values of the axial position of the particle.

18 Claims, 8 Drawing Sheets

(56) References Cited

U.S. PATENT DOCUMENTS

2011/0002530 A1 1/2011 Zhuang et al.
2011/0249866 A1* 10/2011 Piestun ............... G06T 7/0048
382/103

OTHER PUBLICATIONS

Huang, B., et al., "Three-Dimensional Super-Resolution Imaging by Stochastic Optical Reconstruction Microscopy," Science vol. 319, 810 (2008) (4 pages).
Giepmans et al., "The Fluorescent Toolbox for Assessing Protein Location and Function," Science vol. 312, 217 (2006) (8 pages).
Huang et al., "Super-Resolution Fluorescence Microscopy," Annual Review of Biochemistry, vol. 78, 993 (2009) (28 pages).
Pavani, S. R. P., et al., "Three-dimensional, Single-molecule Fluorescence Imaging beyond the Diffraction Limit by Using a Double-helix Point Spread Function," Proceedings of the National Academy of Sciences 106, 2995 (2009) (5 pages).
Shtengel, G., et al., "Interferometric Fluorescent Super-resolution Microscopy Resolves 3D Cellular Ultrastructure," Proceedings of the National Academy of Sciences 106, 3125 (2009) (6 pages).
Whyte, Graeme, and Johannes Courtial, "Experimental Demonstration of Holographic Three-dimensional Light Shaping Using a Gerchberg-Saxton Algorithm," New Journal of Physics 7 (2005) 117 (13 pages).
International Search Report for corresponding International Application No. PCT/EP2012/063511, mailed Sep. 6, 2012 (4 pages).
International Preliminary Report on Patenability for corresponding International Application No. PCT/EP2012/063511, mailed Jul. 12, 2013 (22 pages).

* cited by examiner

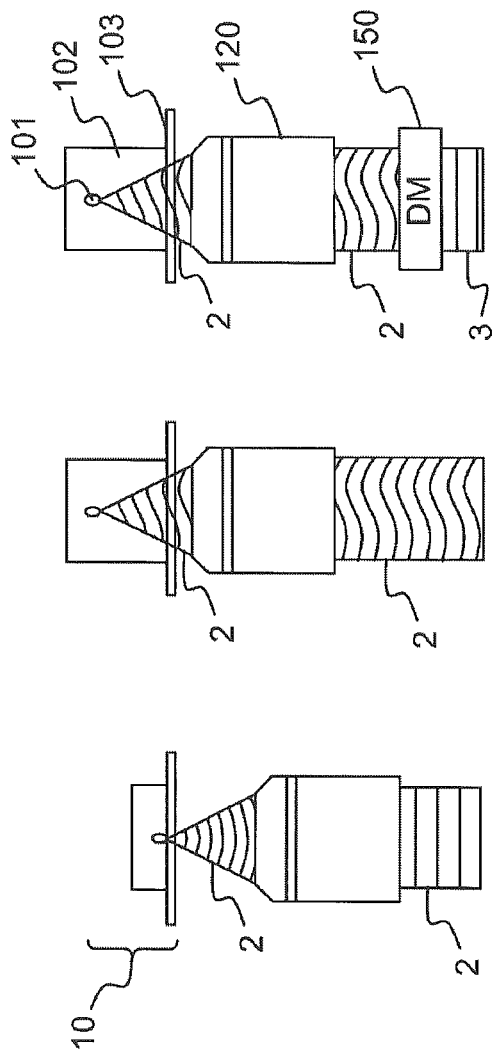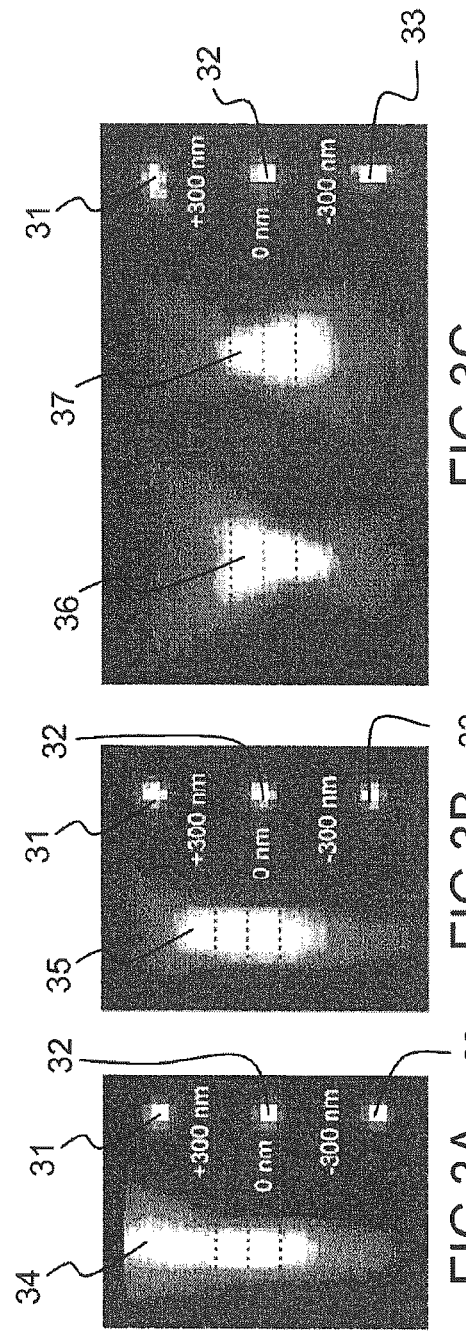

METHOD AND OPTICAL DEVICE FOR SUPER-RESOLUTION LOCALIZATION OF A PARTICLE

CROSS REFERENCE TO RELATED APPLICATIONS

This is a national stage application based on PCT/EP2012/063511, filed on Jul. 10, 2012, which claims priority to French Patent Application No. 1156647, filed on Jul. 21, 2011. This application claims priority to these prior applications and incorporates their disclosures by reference in their entireties.

BACKGROUND

One or more embodiments of the present invention relates to a super-resolution microscopy method and optical device, i.e. with a resolution below the diffraction limit, for three-dimensional localization of one or more particles.

Mankind's understanding of the dynamic architecture of cells is in the process of being completely transformed by technological developments allowing individual molecules to be detected optically in living systems. By virtue of ultrasensitive measuring methods, it is now possible to count, localize and follow the movement of biological molecules in their cellular environment (see for example B. Huang et al. "Super-resolution fluorescence microscopy" Annu Rev Biochem 78, 993 (2009)). In this way, it is possible to analyze the composition, structure and spatial dynamics of molecular complexes with a spatial resolution of a few nanometers and a temporal resolution reaching a millisecond. This opens a window onto a complex molecular organization that could not previously be studied with the microscopy techniques conventionally used in biology and biochemistry. Remarkably, techniques for imaging single molecules have already found applications in fields beyond fundamental research, especially in the important field of DNA sequencing (T. D. Harris et al. "Single-molecule DNA sequencing of a viral genome", Science 320, 106 (2008)). In the medium term, it seems likely that their use will spread to the fields of diagnostics or molecular targeting, fields in which an ultrasensitive detection capacity is a major advantage. There are therefore major scientific and industrial incentives to develop effective approaches to imaging at the scale of individual molecules.

Generally, our cells may be considered to be reactors in which a multitude of biochemical reactions take place between a no less considerable number of reactants (which, for the most part, are proteins). Within a cell, proteins assemble into reactive units that are called macromolecular complexes. The average size of protein assemblies with cellular functions typically ranges from a few nanometers for small complexes to about 100 nanometers for the largest structures such as nuclear pores. Most molecular complexes (nucleosome, RNA polymerase, ribosomes) are between 10 and 30 nm in size. The various interactions between these complexes, and the molecular modifications that result therefrom, form the network of interactions and reactivity that is the physical and chemical medium of all cellular regulation. Analysis of these networks is at the heart of our understanding of cellular processes. Most cellular dysfunctions that result in pathologies are in fact caused by a defect in the interaction or presence of one of the partners of a cellular macromolecular complex. To understand these pathologies, with the aim of effectively combating them, it is indispensable to develop measurement tools capable of providing quantitative information on the stoichiometry (molecular count) and position of protein complexes relative to one another.

At the present time, it is possible to functionalize practically any protein in an organism by adding a genetically encoded tag to it, this tag either being directly fluorescent or being able to react with a soluble fluorescent compound (see for example B. N. Giepmans et al. "The fluorescent toolbox for assessing protein location and function", Science 312, 217 (2006)). These probes are capable of emitting a number of photons comprised between a few hundred thousand and a few million before photobleaching. In other words, tagging with a probe is equivalent to allocating a "photon budget" to a particular protein, which budget may then be used to transfer molecular information to our macroscopic world (for example by way of an amplified CCD camera). Thus, the photons emitted by a fluorescent protein especially allow its position in its cellular environment to be pinpointed with a resolution of a few tens of nanometers, or it to be followed in time, thus allowing its mobility and its interactions with the cellular system to be measured.

The ability to localize molecules is at the heart of pointillist super-resolution microscopies (known by the acronyms PALM for "photo-activated localization microscopy" or STORM for "stochastic optical reconstruction microscopy"). These microscopies, which combine nanoscale localization and control, by photoactivation, of the number of simultaneously active emitters, allow two-dimensional images of cellular samples to be obtained with a resolution of 10-50 nm, far below the conventional diffraction limit (~250 nm in modern epifluorescence microscopes) (B. Huang et al. "Super-resolution fluorescence microscopy" Annu Rev Biochem 78, 993 (2009)). Since the resolution obtained is of the same order of magnitude as the size of the macromolecular assemblies involved, the study of relationships between the spatial organization and the function and structure of the macromolecules becomes possible.

By placing a cylindrical lens on the optical path of the signal, and by calibrating the ellipticity induced in the point spread function (PSF) of the microscope for the individual molecule, 3D STORM microscopy with an axial resolution of about 100 nm, about 2.5 times that in the perpendicular plane, was demonstrated in the laboratory of X. Zhuang at Harvard in 2008 (see for example B. Huang et al. "Three dimensional super-resolution imaging by stochastic optical reconstruction microscopy" Science 319, 810 (2008) or the patent application US 2011/0002530 in the name of the same inventors). With this technique, the axial resolution is related to the break in symmetry of the optical signal along the x- and y-axes as a function of the distance of the fluorophore from the focal plane.

A second method consists in simultaneously imaging the signal from an individual molecule in two axially separate planes. With this simultaneous "biplane" detection, the z-position of a molecule between the two planes may be determined with a precision similar to that achieved with the astigmatic approach (see for example M. F. Juette et al. "Three-dimensional sub-100 nm resolution fluorescence microscopy of thick samples" Nat Methods 5, 527 (2008)); the advantage of this technique is that lateral and axial resolution are not coupled.

However, a limitation that is common to both the cylindrical-lens and biplane techniques is related to residual optical aberrations that deform the PSF and deteriorate the algorithms for laterally and axially localizing the emitting particle. Moreover, the depth (range) over which it is possible to determine the axial position of the molecule is limited (to about 1-2 µm) and is entirely fixed by the opto-mechanical elements of the apparatus, meaning that it is impossible to make rapid adjustments. This is clearly an obstacle to optimum use of the "photon budget", this optimum use depending on the different types of fluorophore used and the biological applications in question.

Lastly, it will be noted that other less commonplace methods have been demonstrated, such as the "double-helix PSF" method (S. R. Pavani et al. "Three dimensional, single-molecule fluorescence imaging beyond the diffraction limit by using a double-helix point spread function" Proc. Natl Acad Sci USA 106, 2995 (2009)) or the "iPALM" method (G. Shtengel et al. "Interferometric fluorescent super-resolution microscopy resolves 3D cellular ultrastructure" Proc. Natl Acad Sci USA 106, 3125 (2009)). Moreover, at the present time the latter technique enables the best localization in z, but at the price of considerable experimental complexity (4pi measuring system and triple interferometric detection of emitted photons) which confines it to marginal use in biological laboratories. In addition, it remains limited to fixed samples.

One or more embodiments of the invention provides a method and a device for three-dimensional localization of emitting particles, or "emitters", with a resolution below the diffraction limit, and in which excellent control of the point spread function of the microscope is obtained, especially allowing measurement reliability to be increased and the use of the available "photon budget" for a given emitter to be optimized.

SUMMARY OF THE INVENTION

One or more embodiments of the invention relates to a super-resolution microscopy method for three-dimensional localization of one or more emitting particles, including:
  forming at least one image of said emitting particle in a detection plane of a detector by way of a microscopy imaging system;
  correcting, by way of a wavefront-modulating device, at least some of the optical defects present between said emitting particle and said detection plane; and
  introducing, via said wavefront-modulating device, a deformation of the wavefront emitted by said emitting particle, allowing a bijective relationship to be formed between the shape of the image of said emitting particle in the detection plane and the axial position of said emitting particle relative to an object plane that is optically conjugated with the detection plane by the microscopy imaging system, in a given range of values of said axial position of the particle, said deformation of the wavefront being controlled by a controller for controlling the wavefront-modulating device.

The use, in the three-dimensional localization method according to one or more embodiments of the invention, of a wavefront-modulating device both to correct optical defects present between the emitting particle and the detection plane, and to control the deformation introduced into the wavefront emitted by the particle, in order to determine the axial position thereof, especially allows sensitivity and precision to be increased through perfect control of the PSF, thereby allowing the available "photon budget" to be adapted to a given emitting particle. Specifically, if the "photon budget", i.e. the number of photons emitted by the emitting particle, is large, it will be possible, while preserving a sufficient detection sensitivity, to introduce a larger-amplitude deformation of the wavefront emitted by the particle so as to widen the depth range over which the emitting particle may be observed. In contrast, with a smaller "photon budget", the quality of the PSF will be promoted to the detriment of the depth range, in order to obtain a satisfactory detection signal, by limiting the amplitude of the deformation introduced into the wavefront emitted by the particle.

In accordance with one or more embodiments, the method may comprise a prior step of analyzing wavefront optical defects present between said emitting particle and said detection plane, by way of a wavefront analyzing device, for example a Shack-Hartmann device. This step might, for example, be carried out when it is possible to introduce, into the sample, a fluorescent bead the emission signal of which is sufficiently strong to allow optical defects to be analyzed, with an analyzer, with good precision.

Alternatively, for example when it is difficult to introduce a fluorescent bead into the sample, the correction of all or some of the optical defects will possibly be carried out iteratively, on the basis of a measure of the image quality of the emitting particle.

In accordance with one or more embodiments, the method furthermore comprises the emission of one or more light beams for exciting at least one emitting particle, allowing said particle to emit a light signal in a given range of wavelengths. The excitation of emitting particles is for example necessary in the case of particles marked with a fluorescent probe.

The controlled deformation is obtained using a combination of Zernike polynomials of even azimuthal order, for example an astigmatism, and more particularly a 3rd-order astigmatism. The introduction of astigmatism allows a bijective relationship to be formed between the shape of the image of the particle and the axial position of the latter by adjusting only one of the coefficients of the Zernike polynomials, when the decomposition of the wavefront is based on these polynomials. It is then possible, by adjusting the amplitude of the astigmatism introduced, to vary the axial-position range of interest of the particle.

In one or more embodiments, the method may also comprise a step of focusing dynamically on an emitting particle, said dynamic focus being obtained by controllably defocusing the wavefront emitted by said particle by way of said wavefront-modulating device. The use of the wavefront modulator in the three-dimensional localization method according to one or more embodiments of the invention thus makes it possible to access other functionalities, and will for example be employed to follow particles without mechanically moving the sample relative to the microscopy device.

One or more embodiments of the invention relates to a wavefront-controlling device intended to be connected to a super-resolution microscopy system for localizing an emitting particle, the microscopy system comprising a microscope equipped with an optical imaging system and a detector. Such a wavefront-controlling device is intended to be connected to a prior-art super-resolution microscopy system, in order to implement the method according to the first aspect. The wavefront-controlling device comprises:
  a relay optical system for optically conjugating an entrance plane and an exit plane that are intended to be coincident with an image plane of said optical imaging system of the microscope and a detection plane of the detector, respectively;
  a device for spatially modulating wavefronts, comprising a correction plane and allowing the wavefront emitted by said emitting particle to be modulated when said control device is connected to the super-resolution microscopy system;

an optical system allowing an entrance pupil plane of the control device to be optically conjugated with said correction plane, said pupil plane being intended to be coincident with the exit pupil of the optical imaging system of the microscope; and controller for controlling said device for spatially modulating wavefronts, allowing, when the wavefront-controlling device is connected to the super-resolution microscopy system, at least some of the optical defects present between said particle and said detection plane to be corrected and a controlled deformation of the wavefront to be introduced, allowing a bijective relationship between the shape of the image of said emitting particle in the detection plane and the axial position of said emitting particle relative to an object plane, which is optically conjugated with the detection plane, to be formed in a given range of values of said axial position of the particle.

Thus, it is possible to form a "module" able to be connected to any super-resolution microscopy system in order to improve the sensitivity and increase the functionalities thereof. Such a wavefront-controlling device will possibly and advantageously comprise mechanical interfaces for connection to the super-resolution microscopy system, between the microscope and the detector of said microscopy system.

For example, the device for spatially modulating light is a deformable mirror.

In accordance with one or more embodiments, the wavefront-controlling device furthermore comprises a device for analyzing optical defects, for example a Shack-Hartmann analyzer, which device is connected to said controller. The wavefront analyzer will possibly allow the prior step of analyzing optical defects to be carried out.

One or more embodiments of the invention relates to a super-resolution microscopy device for three-dimensional localization of one or more emitting particles, comprising:
  a system for imaging said emitting particle in a detection plane of a detector;
  a device for spatially modulating wavefronts, allowing the wavefront emitted by said emitting particle to be modulated;
  controller for controlling said device for spatially modulating wavefronts, allowing at least some of the optical defects present between said particle and said detection plane to be corrected and a controlled deformation of the wavefront to be introduced, allowing a bijective relationship between the shape of the image of said emitting particle in the detection plane and the axial position of said emitting particle relative to an object plane, which is optically conjugated with the detection plane by the microscope imaging system, to be formed in a given range of values of said axial position of the particle.

In accordance with one or more embodiments, the device for three-dimensional localization according to the third aspect will possibly be a modular device, with on the one hand a super-resolution microscopy system for localizing an emitting particle, of the type comprising a microscope equipped with an optical imaging system and a detector, and on the other hand a wavefront-controlling device according to the second aspect connected to said microscopy system. In this case, said imaging system of the device according to the third aspect will possibly comprise the optical imaging system of the microscope and the relay optical system of the wavefront-controlling device according to the second aspect. Alternatively, the three-dimensional localization device according to the third aspect will possibly have a non-modular design, without relay optics.

In both cases, the device for spatially modulating wavefronts, of the three-dimensional localization device according to the third aspect, advantageously contains a correction plane that is optically conjugated with the pupil of said imaging system. For example, the device for spatially modulating light is a deformable mirror. In the case of a modular device, the correction plane is advantageously conjugated with the exit pupil of the optical imaging system of the microscope.

In accordance with one or more embodiments, the device for three-dimensional localization according to the third aspect furthermore comprises a device for analyzing optical defects, for example a Shack-Hartmann analyzer, which device is connected to said controller. Alternatively, said controller ensures the correction of all or some of the optical defects iteratively, on the basis of a measure of the quality of the images formed of the emitting particle.

In accordance with one or more embodiments, the device for three-dimensional localization according to the third aspect furthermore comprises a device for emitting one or more light beams for exciting at least one emitting particle, allowing said particle to emit a light signal in a given range of wavelengths.

The detector is a matrix detector, for example an EMCCD amplified camera.

BRIEF DESCRIPTION OF THE DRAWINGS

FIGS. 2A to 2C show the reduction in the quality of the point spread function caused by aberrations due to the sample, and their correction by way of a device in accordance with one or more embodiments of the invention;

FIGS. 3A to 3C show the super-resolution microscopy point spread function for a fluorescent bead in three configurations: without correction, with correction, and with correction and controlled introduction of astigmatism in accordance with one or more embodiments of the invention;

For the sake of legibility, identical elements have been given the same references in the various figures.

DETAILED DESCRIPTION

Figure 1A:
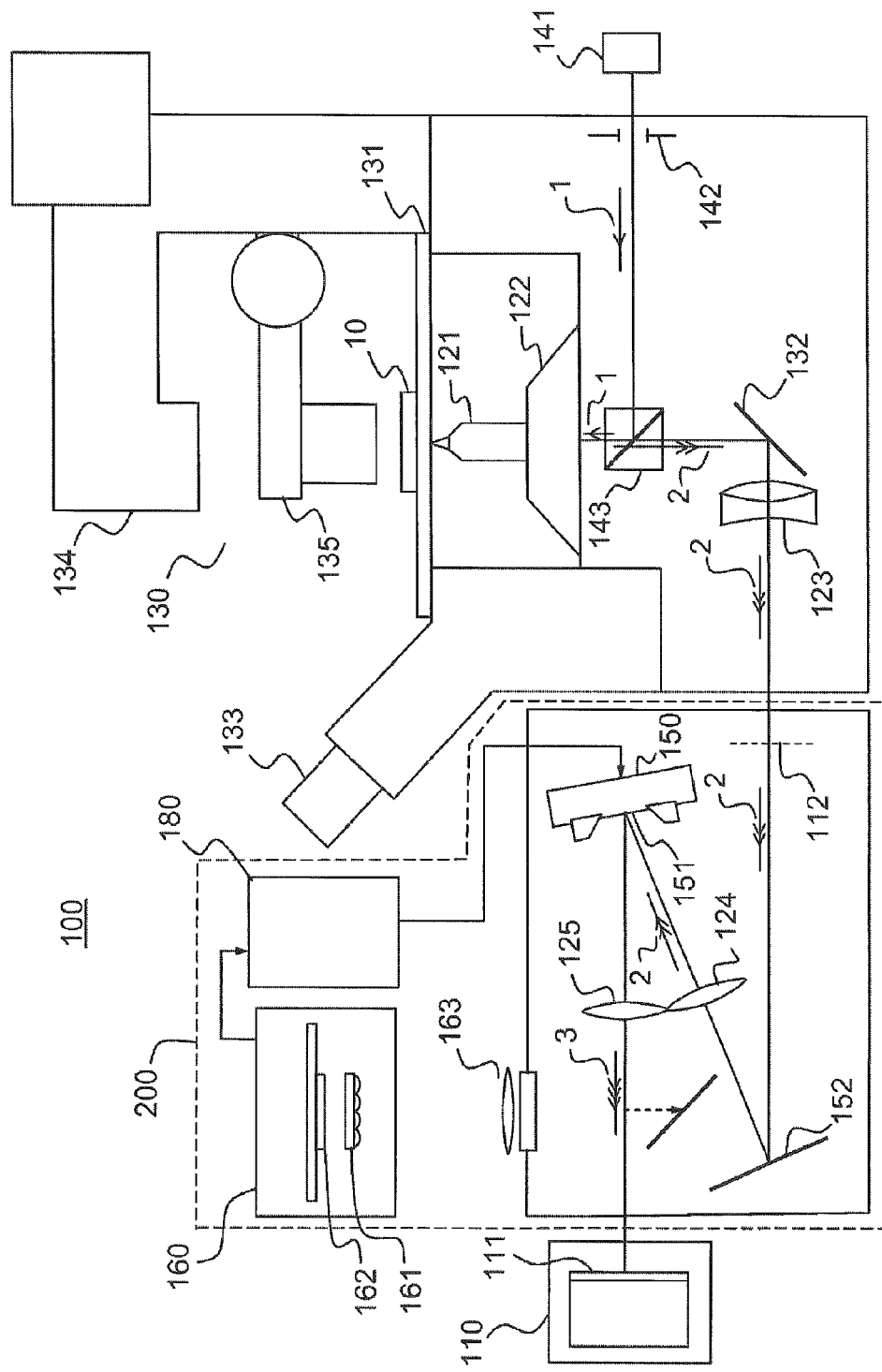
FIGS. 1A and 1B show a device for 3D localization of particles in accordance with one or more embodiments of the invention at two steps of the localization method.
Figure 1B:
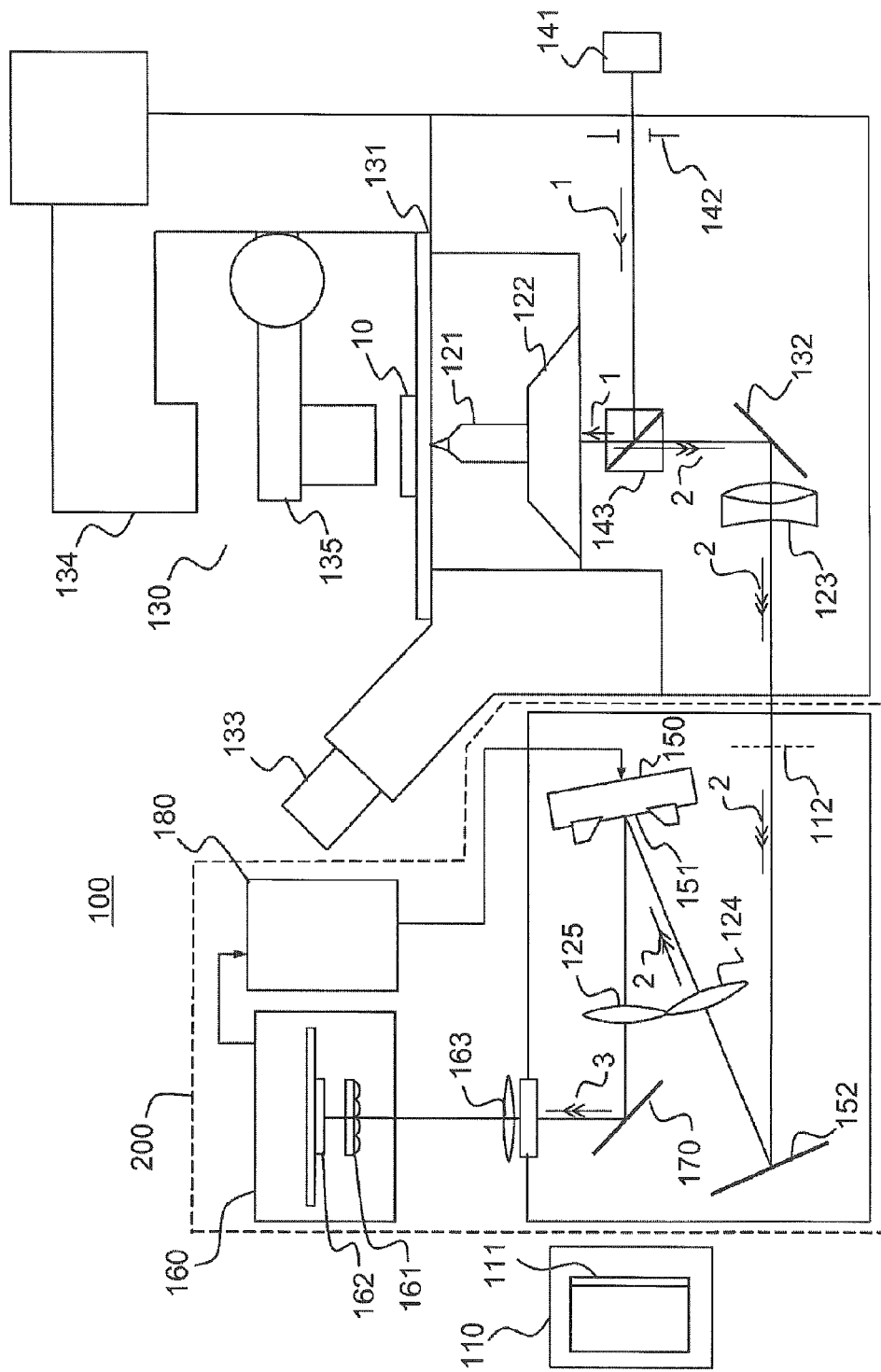

FIGS. 1A and 1B illustrate a device 100 for three-dimensional localization of one or more emitting particles according to one example of the invention.

The expression "emitting particle" is understood in the present description to mean any particle capable of emitting a light signal, either spontaneously or by activation, for example by way of a light source (photoactivation). The particles are, for example, reactive units or macromolecular complexes formed by proteins or assemblies of proteins, tagged, using known techniques, with a probe capable of emitting a light signal, for example a fluorescent probe. Average sizes typically range from a few nanometers for small complexes to about 100 nanometers for the largest structures. Most molecular complexes are between 10 and 30 nm in size. In any case, it is desired to localize emitting particles of smaller size than the diffraction limit of the optical system used to form an image thereof. The particles that it is desired to localize are contained in a supporting medium, a biological medium for example, that may be liquid or solid or take the form of a gel for example. The supporting medium may be arranged directly on a sample holder, deposited on a plate, or held between two plates, glass plates for example. The term "sample" (10, FIGS. 1A, 1B) is used to designate the supporting medium and the emitting particles contained therein, and the one or more holding plates if required.

The three-dimensional localization device 100 in the example in FIGS. 1A and 1B is modular and comprises a microscope 130, a detector 110 and a wavefront-controlling device referenced 200. In the example in FIGS. 1A and 1B, the device 100 comprises an imaging system able to form an image of the emitting particle on a detection plane 111 of a detector 110, advantageously a matrix detector, for example an amplified camera of the electron multiplying charge-coupled device (EMCCD) type. In this example, the imaging system comprises a microscope objective 121, for example corrected for an infinite-focus optical working configuration, associated with an objective 123 called the tube lens, allowing an image to be formed on an intermediate detection plane 112. The microscope objective/tube lens assembly forms a conventional microscope optical system. Furthermore, the imaging system comprises relay objectives 124, 125 allowing the image of the intermediate detection plane 112 to be formed on the detection plane 111 of the detector 110. Because of the very small size of the emitting particles (smaller than the diffraction limit of the imaging system), the image, which is the convolution of the object with the point spread function or PSF of the imaging system, is here substantially equivalent to the point spread function. The microscope objective 121 is advantageously fitted to a carousel 122 able to receive a plurality of said objectives in order to allow the choice of the microscope objective to be matched to the desired enlargement. A motorized platform 131 allows a sample holder (not shown), which is intended to receive the sample 10, to be moved in an x-y plane perpendicular to the optical axis of the microscope objective. A mechanical axial focusing device (not shown) allows the axial position of the sample to be adjusted relative to the object focal plane of the microscope objective 121, and thus the region of interest to be imaged. The sample holder, the motorized platform, the axial focusing device, the microscope objective 121 and the tube lens 123 are arranged in a known type of microscope body 130. The microscope body is advantageously adapted to what is called fluorescence microscopy and comprises a device for illuminating the sample, especially comprising a source 141 for emitting one or more light beams 1 for exciting emitting particles. In the example in FIGS. 1A and 1B, the illuminating device furthermore comprises a dichroic mirror 143 allowing the exciting light beam 1 to be reflected toward the objective 121 (so-called epifluorescence microscopy). Advantageously, a field diaphragm 142 may be provided to limit the illuminated field to a region of interest of the sample. In this example, the emission signal 2 of the emitting particles is transmitted by the dichroic mirror 143 then directed toward the tube lens 123 and the detector by way of a directing mirror 132. Moreover, the microscope body may comprise, in the conventional way, an eyepiece 133 and a source for illuminating the sample 134, which source is associated with a condenser 135. The eyepiece allows the sample, which is illuminated from above by the illumination source 134, to be positioned by eye initially. The directing mirror 132 may be fitted to a movable device allowing the axis of observation of the sample to be switched toward the eyepiece when it is desired to observe the sample by eye, or toward the detector 110 in order to continue with localization of the emitting particles. Furthermore, the device 100 comprises a device 150 for spatially modulating wavefronts and controller 180 for controlling said spatially modulating device, the operation of which is described in detail below.

In the three-dimensional localization device according to one or more embodiments of the invention, such as shown in FIGS. 1A and 1B, the device 150, for example a deformable mirror, for spatially modulating wavefronts allows the wavefront 2 emitted by said emitting particle and transmitted to a modulating plane 151 of the device 150, for example by way of the mirror 152, to be modulated. Next, the modulated wave 3 is directed toward the detection plane 111 of the detector 110. Advantageously, the modulating plane 151 is optically conjugated with the exit pupil of the optical imaging system of the microscope, comprising the microscope objective 121 and the tube lens 123. In the example of a modular system in which a wavefront-controlling device 200 is intended to be connected to a super-resolution microscopy system 130, the modulating plane 151 will be optically conjugated with an entrance pupil plane of the controlling device, itself intended to be coincident with an exit pupil plane of the optical imaging system of the microscope 130. In the example in FIGS. 1A and 1B, the optical system 124 allows the pupil planes to be conjugated. In these figures, the exit pupil plane of the optical imaging system of the microscope is a virtual plane, projected to infinity. The controller 180 of the device for spatially modulating wavefronts allows at least some of the optical defects present between the emitting particles and the detection plane 111 to be corrected. It also controls the modulating device 150 in order to introduce a controlled deformation of the wavefront. The aim of this controlled deformation is to establish a bijective relationship between the shape of the image of the emitting particle in the detection plane 111 and the axial position of the emitting particle relative to an object plane, defined as the plane optically conjugated with the detection plane 111 by the microscopy imaging system, as will be described in greater detail below.

In one embodiment, all or some of the optical defects present between the emitting particles and the detection plane are corrected by way of a device 160 for analyzing optical defects, which device is connected to the controller 180. The device 160 for analyzing optical defects is, for example, a Shack-Hartmann device comprising a matrix of microlenses forming an analysis plane 161, and a matrix detector 162 substantially positioned in a focal plane of said microlenses. Advantageously, the analysis plane 161 is optically conjugated with a pupil of the imaging system. The device for analyzing optical defects is, for example, the Imagine Optic® HASO® 3-32. In a first step of the method for three-dimensional localization of emitting particles, optical defects present between the medium of the particles and the detection plane are analyzed by way of the analyzer 160. To do this, a retractable mirror 170 allows the beam 2 emitted by the one or more emitting particles to be transmitted to the analyzer 160 (FIG. 1B). In practice, the analysis of optical defects may be carried out by way of a fluorescent bead inserted into the sample, forming an "artificial star" the intensity of the fluorescence of which is sufficient to allow optical defects to be analyzed with good precision. The controller 180 then calculates the optical defects present in the imaging system from measurements carried out by the analyzer. In a second step of the localization method, illustrated in FIG. 1B, the controller transmits a correction control signal to the modulating device 150, for example an Imagine Eyes® Mirao 52-e deformable mirror, in order to correct as best as possible the measured optical defects, and to incorporate the controlled deformation of the wavefront. In this step, the position of the retractable mirror allows the modulated beam 3 to be transmitted to the detection plane 111.

Alternatively, especially when it is difficult or impossible to insert a fluorescent bead into the medium of the emitting particles, for example when the medium is a biological tissue or a living system, optical defects may be corrected using an iterative correction method based on images of the emitting particles and a measure of the quality of the images. In this case, the controller determines the correction control signal to transmit to the modulating device 150 on the basis of information generated by the detector 110.

Thus, in the example in FIGS. 1A and 1B, the three-dimensional localization device is formed from three main modules comprising the microscope 130, the detector 110 and a wavefront-controlling device, referenced 200 in FIGS. 1A and 1B and especially comprising the wavefront-modulating device 150, the controller 180, the relay objectives 124, 125 and optionally the device 160 for analyzing optical defects. The controlling device 200 may also comprise mechanical interfaces (not shown) allowing said wavefront-controlling device to be connected on the one hand to the "microscope" module 130, and on the other hand to the "detector" module 110. Such a modular arrangement has the advantage of being adaptable to existing super-resolution microscopy systems.

In one embodiment, the three-dimensional localization device may be formed from a single module. In this case, the relay objectives 124, 125 are no longer necessary since their function is especially to convey the image formed on the intermediate focal plane 112 to the detection focal plane 111. In the case where the device is not designed to be fitted to an existing microscopy system but instead forms part of a complete three-dimensional localization device, the design constraint relating to the existence of the intermediate focal plane no longer exists, and the design may differ from that shown in FIGS. 1A and 1B. In particular, the optical system allowing the emitting particle to be imaged in the detection plane 111 of the detector 110 may be arranged in any number of optical configurations, known to those skilled in the art.

FIGS. 2A to 2C schematically illustrate the deterioration in the quality of the point spread function caused by aberrations due to the sample, and their correction by way of a device according to one or more embodiments of the invention. As in FIGS. 1A and 1B, the beam emitted by an emitting particle 101 contained in a medium 102 arranged between two glass strips 103, only one of which is shown in FIG. 2, is referenced 2, the assembly 101, 102, 103 forming the sample 10. The imaging device forming the image of the emitting particles on the detection plane (not shown in FIG. 2) is referenced 120. In the example in FIG. 2A, the wavefront 2 is not deteriorated by the sample because the object focal plane of the imaging device is located on the surface of the sample. In the example in FIG. 2B, the emitted beam 2 passes through part of the medium 102 of the sample 10; inhomogeneities in the refractive index of the material shift the phase of the beam, leading to the quality of the resulting point spread function (PSF) being degraded. In the example in FIG. 2C, a device 150 for modulating the phase of the wavefront (for example a deformable mirror DM) allows defects due to the sample to be corrected. The modulated beam 3 is corrected for aberrations introduced by the sample and the quality of the PSF is restored. In practice, many factors are liable to contribute to degradation of the PSF and a loss of resolution. These factors comprise not only the aberrations introduced by the sample itself, but also optical defects introduced by all of the optical components of the imaging system.

Super-resolution microscopy localization performance is very dependent on the optical quality of the beams emitted by the emitting particles and received by the detector; however, this optical quality is degraded by optical aberrations due to the studied sample, as was illustrated by way of FIGS. 2A to 2C, but also by aberrations due to all the components of the imaging system, especially the microscope objective, the immersion liquid (i.e. oil) in the case of an immersion objective, the tube lens, the objectives 124, 125 but also any filters, beam splitters or other components of the imaging system. In practice, the modification of the focal spot (PSF) that makes axial localization of the emitter possible in prior-art PALM/STORM systems is obtained by addition of a very small amplitude astigmatism (typically with a peak-to-valley amplitude of between 200 and 400 nm i.e. about lambda/4 to lambda/2, where lambda is the emission wavelength of the emitting particles). However, the imaging system introduces optical aberrations of the same order of magnitude, and the sample may induce aberrations of notably larger amplitude. It will be understood that this being the case, the modification of the shape of the PSF cannot be adequately controlled because this shape is "polluted" by a parasitic modification that has an arbitrary shape and an amplitude that is comparable to or larger than the desired shape. Introducing a wavefront-modulating device allowing all or some of the optical defects of the imaging system between the medium containing the emitting particles and the detection plane to be corrected will thus allow the precision with which particles can be localized to be considerably increased.

Once the system has been corrected, as well as possible, for optical defects, the wavefront-modulating device associated with the controller furthermore allows a controlled deformation, for example an astigmatism, to be introduced and the shape of the PSF of a point emitter to be modified depending on its distance from the focal plane.

FIGS. 3A to 3C show experimental images showing the super-resolution microscopy point spread function (PSF) of an emitting particle found by a fluorescent bead in three configurations: without correction (FIG. 3A), with correction (FIG. 3B) and with correction and controlled introduction of astigmatism (FIG. 3C) for various axial positions of the bead. The measurements in FIGS. 3A to 3C are obtained with a fluorescent bead of 40 nm diameter arranged in a phosphate buffered saline (PBS) buffer and deposited on a glass strip. The device for localizing the bead is a device of the type shown in FIGS. 1A and 1B. The illumination source 141 emits an exciting beam (1) at 590 nm, the beam (2) emitted by the fluorescent bead being emitted at 605 nm. The microscope used for these measurements is a Nikkon Eclipse TI® total internal reflection fluorescence microscope with a 100× magnification oil immersion objective having a numerical aperture of 1.49. The wavefront analyzer 160 used is a Shack-Hartmann Imagine Optic® HASO® 3-32, and the wavefront modulator an Imagine Eyes® Mirao 52-e deformable mirror. The matrix detector is an amplified EMCCD camera, more precisely, in this example, an Andor® iXon® DU897 camera. In these figures, the images 31, 32, 33 respectively show the PSFs measured on the detection plane (x-y plane transverse to the optical z-axis) for three axial positions of the bead (+300 nm, 0 nm and −300 nm, respectively) relative to the object plane of the imaging system, this plane being defined as the plane optically conjugated with the detection plane by the imaging system. The images 34 and 35 show the PSFs measured in an x-z plane containing the optical axis, these images being obtained by reconstructing a series of images measured in the detection plane for various axial positions. Without introduction of astigmatism (FIGS. 3A, 3B), a substantially constant PSF is observed as a function of the axial position of the bead. However, an improvement in the quality of the PSF is observed with correction (FIG. 3B), thereby allowing the light rays emitted by the fluorescent bead to be concentrated on a smaller number of detector pixels, therefore allowing sensitivity to be improved. The images 36 and 37 in FIG. 3C show PSFs measured in the x-z and y-z planes, respectively. The observed asymmetry is characteristic of the axial position of the bead.

Figure 4A:
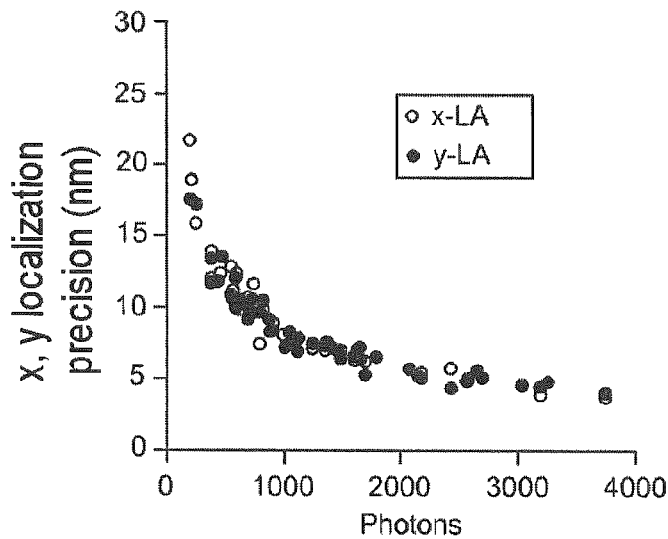
FIGS. 4A to 4C show lateral-measurement precision in the experimental configurations of FIGS. 3A to 3C.
Figure 4B:
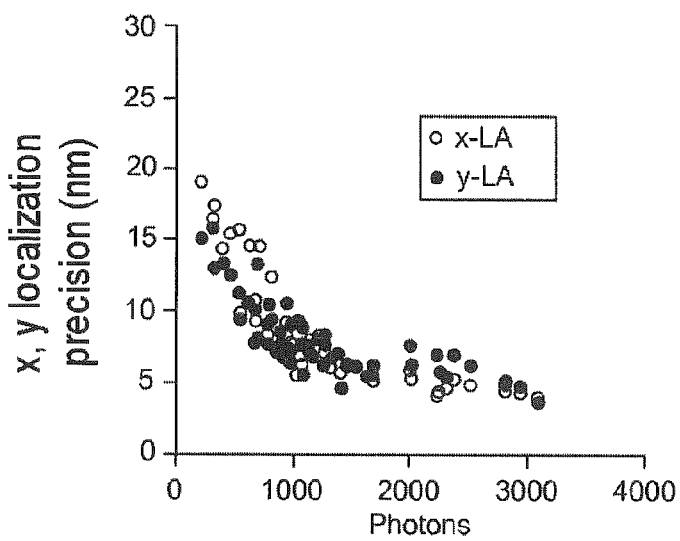
Figure 4C:
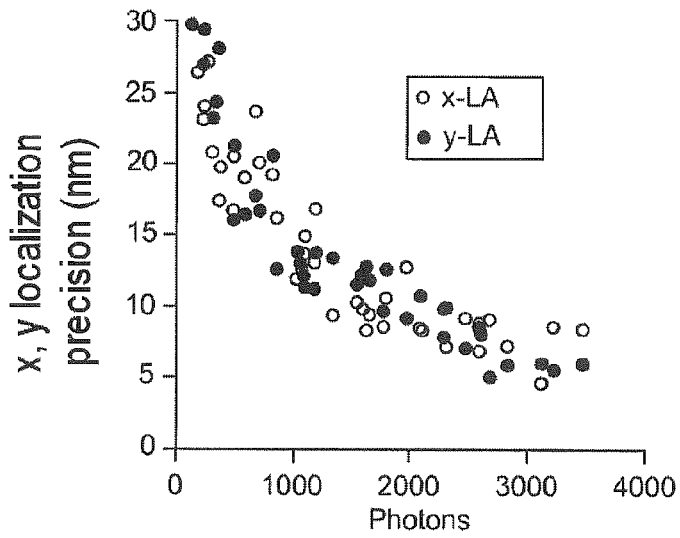

FIGS. 4A to 4C show the precision in x and in y (denoted x-LA and y-LA, respectively) of measurements carried out, in the experimental configurations of FIGS. 3A to 3C (without correction, with correction, with correction and controlled introduction of astigmatism), for a given axial position of the bead, as a function of the number of photons. The precision is obtained by measuring the deviation in the measured values of the lateral dimensions of the PSF in the detection plane over a given number of measurements, typically about 5000. It is remarkable to note that the precision of the lateral localization remains almost unchanged between optical configurations with and without correction (FIGS. 4A and 4B). Specifically, despite the loss of light flux due to the presence of the deformable mirror and the additional lenses 124, 125, the correction of aberrations allows the precision of the lateral localization to remain substantially unchanged. The curve 4C shows a very small loss in lateral precision despite introduction of the astigmatism that will allow additional information relating to the axial position of the bead to be gathered.

Figure 5A:
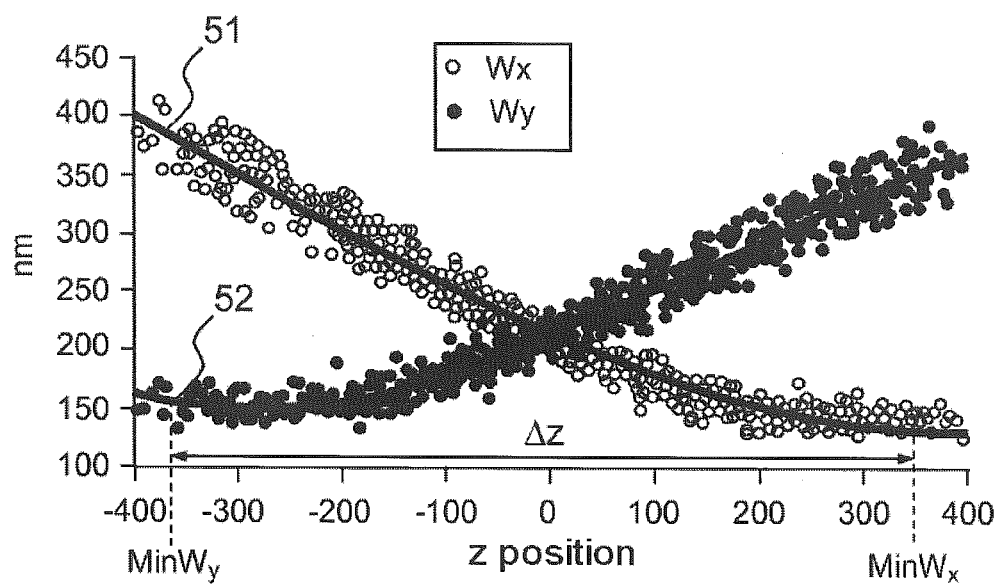
FIGS. 5A and 5B show experimental and modeled curves of functions giving the lateral dimensions of the point spread function as a function of the axial position of the bead, in the presence of controlled astigmatism (experimental conditions of FIG. 3C)

FIG. 5A shows experimental measurements showing the lateral dimensions of the PSF (denoted $W_x$ and $W_y$ for lateral dimensions along the x-axis and y-axis, respectively) once a 0.4 μm P-V (peak-to-valley) astigmatism has been introduced, after correction of aberrations, as a function of the axial position of the bead. These curves are obtained with experimental configurations similar to those of FIG. 3C. These measurements are approximated by curves, 51 and 52, corresponding to the measurements $W_x$ and $W_y$, respectively, and corresponding perfectly to the expected theoretical curves. If reference is made to FIG. 3C, the lateral x-dimension of the PSF is observed to decrease between −400 nm and +400 nm (image 36), which decrease appears in the curve 51 (FIG. 5A) giving the lateral x-dimension as a function of the axial z-position of the bead. In contrast, an increase in the lateral y-dimension of the PSF is observed (image 37), which increase is seen in the curve 52 (FIG. 5A) giving the lateral y-dimension as a function of the axial z-position of the bead. It is remarkable to note that the curves 51 and 52 exhibit very good symmetry with respect to the point z=0 corresponding to the position of the object focal plane. This symmetry is a result of the prior correction of the aberrations due to all of the components of the imaging system present between the emitting particle and the detection plane, and allows the axial location of the particle to be determined with excellent precision. The curves 51 and 52 exhibit a minimum for each of the lateral dimensions, denoted Min $W_x$ and Min $W_y$, respectively, beyond which minimums the lateral x- and y-dimensions of the PSF increase. It may be shown that for bead axial positions beyond these minimums, the localization precision greatly decreases because of the increase in the lateral dimensions of the PSFs in both x and y. Thus, it is possible to define the axial distance $\Delta z$ between these two minimums as the localization range of the emitting particle in z.

Figure 5B:
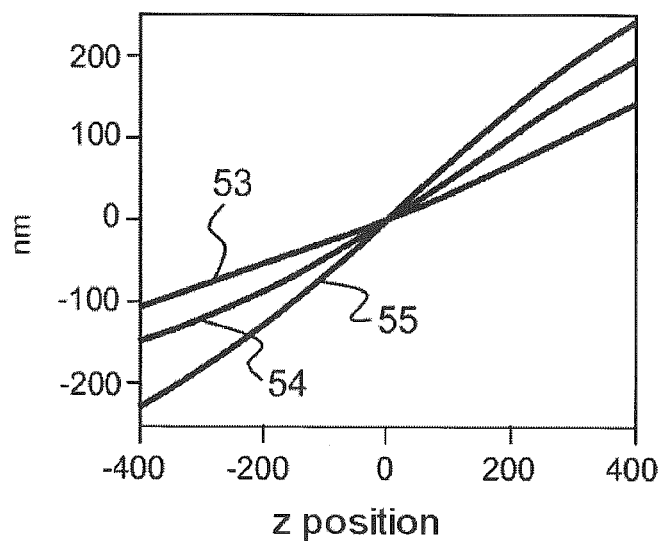

Thus, FIG. 5B illustrates curves 53, 54 and 55 showing the values of the differences between the lateral x- and y-dimensions ($W_x-W_y$) for three astigmatism values, 0.2, 0.3 and 0.4 μm P-V, respectively. Considering the difference in the lateral dimensions $W_x-W_y$ with a view to determining the axial position of the bead, not only is a bijective relationship formed between the measured value and the axial position of the bead, but it is also possible to avoid an effect that is encountered when the particle is not a perfect point source, i.e. when the size of the particle is no longer negligible relative to the PSF. Because of the bijective relationship that exists between the difference $W_x-W_y$ and the axial position of the bead relative to the object focal plane (corresponding to z=0 in FIG. 5B), it is possible to calibrate the localization system for subsequent emitting particle localization measurements. A more rapid and larger variation in the function $W_x-W_y$ is observed as the astigmatism increases, which is explained by a larger variation in the shape of the PSF. However, for astigmatism values beyond a certain threshold, the PSF will spread over too many pixels to obtain a signal-to-noise ratio that is large enough to allow a good 3D localization of the emitting particle. It is therefore advantageous to control the amplitude of the deformation introduced by the wavefront-modulating device depending on the available "photon budget", which depends on the nature of the emitting particles.

Figure 6A:
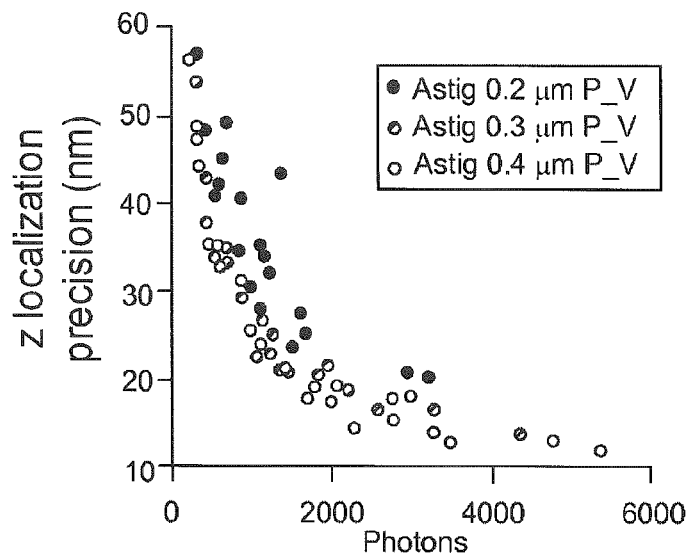
FIGS. 6A to 6C show experimental curves showing the precision of the axial position of the bead (experimental conditions of FIG. 3C), for various astigmatism values, as a function of the number of photons and of the axial position of the bead, and curve showing the measured axial position as a function of the movement of the bead in the sample.
Figure 6B:
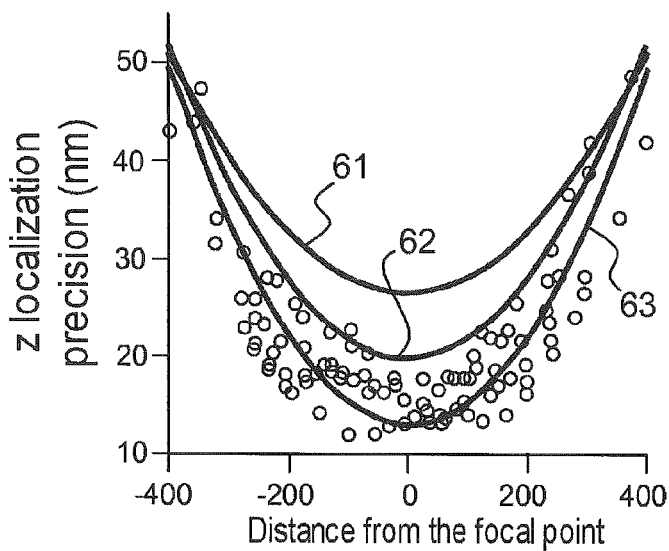
Figure 6C:
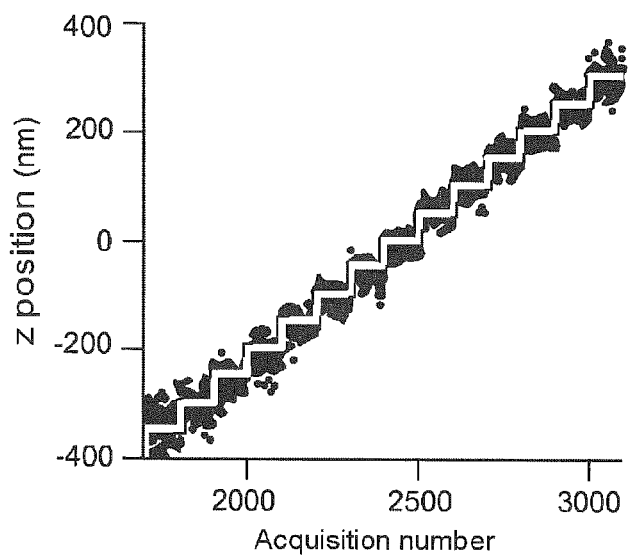

FIGS. 6A to 6C show experimental curves showing the precision of the measurement of the axial position of the bead (experimental conditions of FIG. 3C) for various astigmatism values, as a function of the number of photons (FIG. 6A) and as a function of the axial position of the bead (FIG. 6B), and a curve showing the axial position of the bead measured as a function of the acquisition number, the position of the bead changing by 50 nm every 100 acquisitions (FIG. 6C). FIG. 6A confirms that precision increases with the number of photons. Moreover, the precision of the axial localization of the bead is better for larger astigmatism values, the difference in the measured values of the lateral dimensions of the PSF in theory being larger. This tendency is confirmed by FIG. 6B, in which the points represent experimental measurements obtained with an astigmatism of 0.4 μm P-V whereas the curves represent approximations calculated for 3 astigmatism values, as a function of the axial z-position of the bead. In FIG. 6C, a perfect correlation is observed between the values of the axial position of the bead measured (measurements represented by points) with an astigmatism of 0.4 µm P-V and the theoretical curve (solid line).

Figure 7:
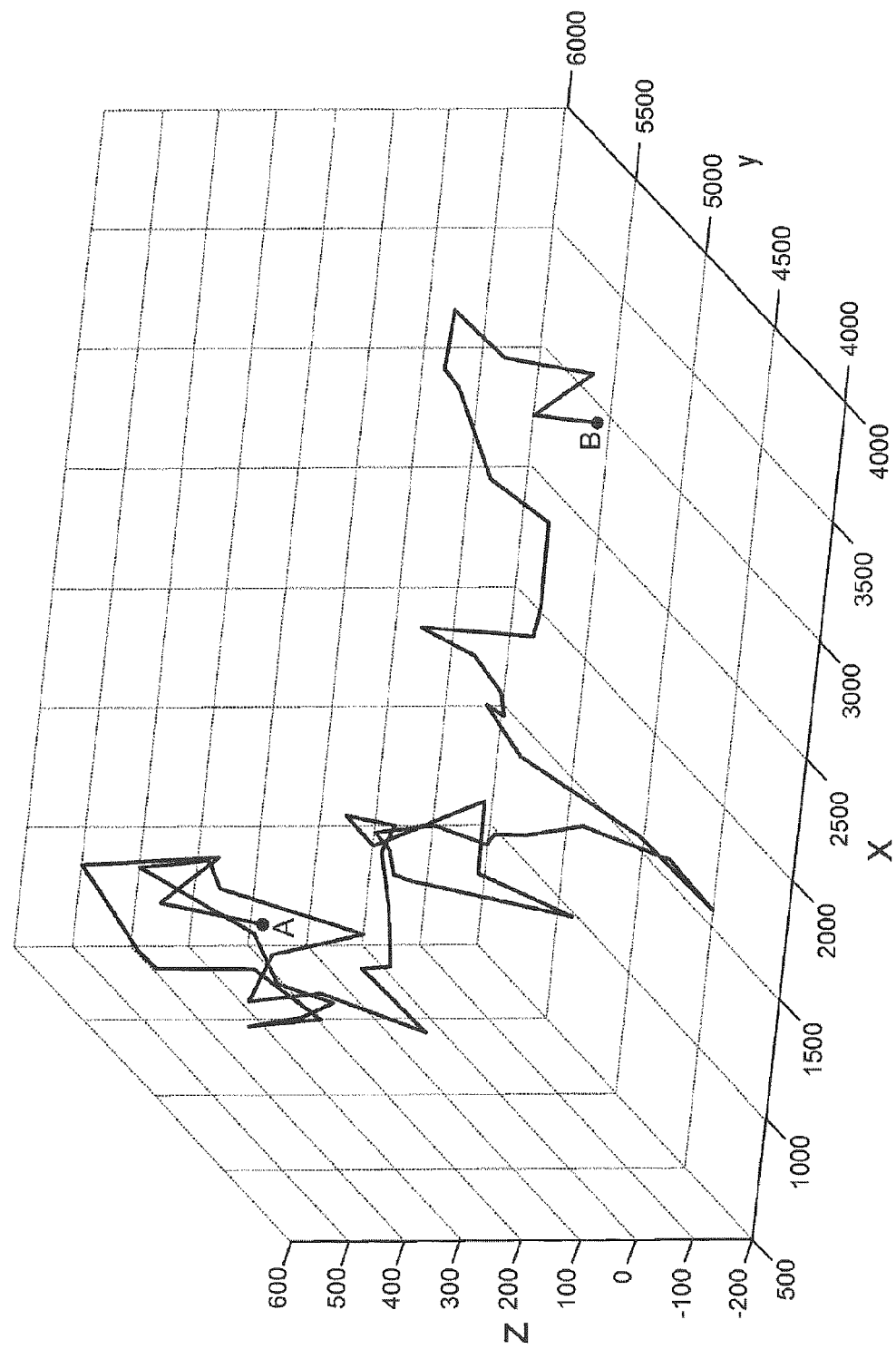
FIG. 7 shows an experimental curve showing the movement of a transmembrane protein obtained with a localization method according to one embodiment of the invention.

FIG. 7 shows the experimental results obtained by tracking a quantum dot attached to a transmembrane protein diffusing across the membrane of a HeLa cell, a cellular line frequently used in cellular biology and in medical research, in three dimensions. The quantum dot behaves as a fluorescent probe that may be tracked over time. The experimental points are obtained with a device identical to that described with reference to FIGS. 3A to 3C, the wavefront-modulating device allowing, for the measurement of the axial position of the quantum dot, a controlled astigmatism of 0.4 µm P-V to be introduced after aberration correction. The path of the quantum dot is recorded then plotted in 3D, between a point A and a point B, the acquisition frequency between two points being 10 Hz. These experimental results for quantum dots fixed to proteins contained in biological media show the excellent precision attainable by virtue of the three-dimensional localization method according to one or more embodiments of the invention.

FIG. 7 shows the application of the method to path measurement. Other applications, such as three-dimensional reconstruction of a structure, for example of a neuron membrane, are possible when PALM or STORM technologies are used to determine the x and y position of the emitting particles attached to the macromolecular complexes, and the controlled wavefront modulation such as described above is used for axial localization (in z) of the emitting particles.

Spatial modulation of the wavefront emitted by the emitting particles especially has the advantages described above, regarding the improved precision and regarding the optimization of the available "photon budget" via the choice of the controlled deformation of the wavefront.

In particular, although, in the examples described, a controlled astigmatism was introduced, other controlled deformations are possible, provided that they form a bijective relationship between the shape of the PSF and the axial position of the particle by breaking the axial symmetry of the PSF.

For example, any deformation of the wavefront based on a combination of Zernike polynomials of even azimuthal order allows, as is known, an axial asymmetry to be introduced into the PSF. These may be Zernike polynomials of 2nd azimuthal order, i.e. all polynomials in $\cos(2\theta)$ or $\sin(2\theta)$. Third-order astigmatisms in $r^2 \cos(2\theta)$ and $r^2 \sin(2\theta)$ are the most common, but it may also be envisioned to use any higher-order astigmatism, such as, for example, astigmatisms of the 5th order in $(4r^2-3)r^2 \cos(2\theta)$ and $(4r^2-3)r^2 \sin(2\theta)$ and astigmatisms of the 7th, 9th, 11th order, etc. It is also possible to envision using any combination of Zernike polynomials of 4th azimuthal order. These polynomials form part of the tetrafoil family, which, for example, includes polynomials in r4 $\cos(4\theta)$ and r4 $\sin(4\theta)$.

Figure 8B:
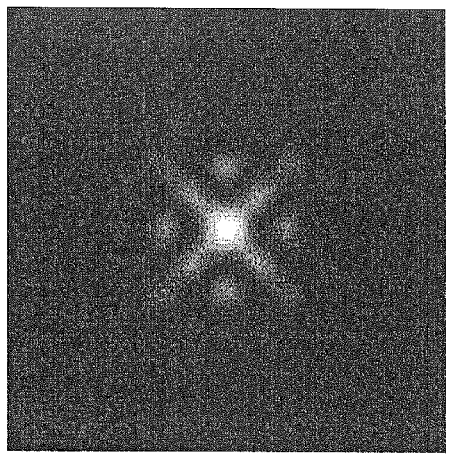
FIG. 8A to 8D, respectively, show the representation of the phase of one example of a tetrafoil wavefront (FIG. 8A), and the shape of the resulting PSF of the wavefront shown in FIG. 8A in a plane preceding the plane of best focus (FIG. 8B), in the plane of best focus (FIG. 8C) and in a plane following the plane of best focus (FIG. 8D).
Figure 8D:
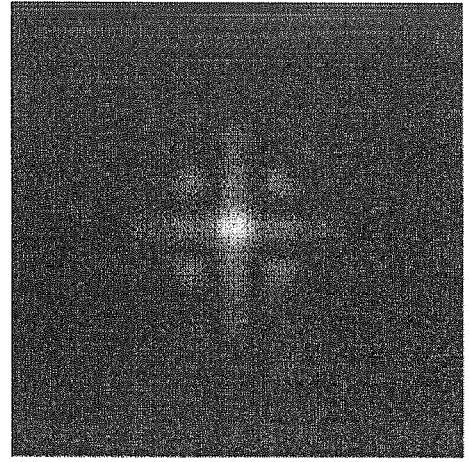
Figure 8A:
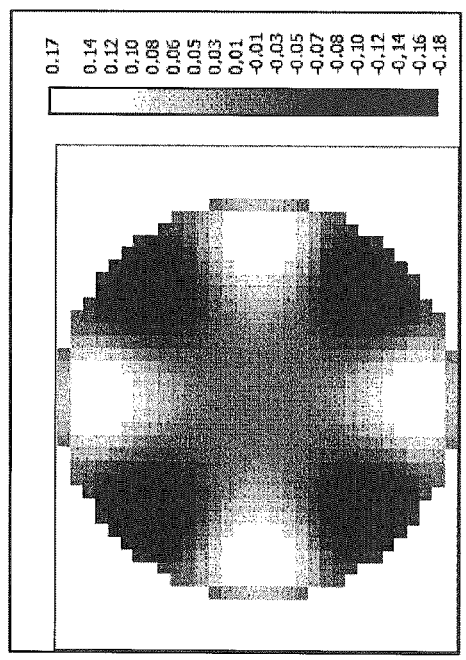

By way of example, FIG. 8A illustrates the phase $\phi(r,\theta)$ of a tetrafoil wavefront, expressed, in polar coordinates, by the equation:

$$\phi(r,\theta)=0.2*r^4*\cos(4*\theta)-0.2*(6*r^2-5)*r^4*\cos(4*\theta)$$

Figure 8C:
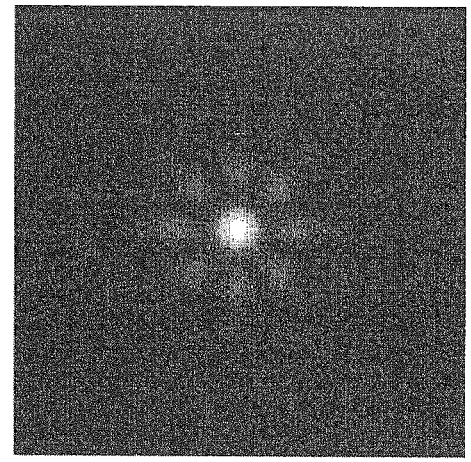

FIGS. 8B to 8D illustrate the shape of the PSF, for a wavelength of 500 nm, before the plane of best focus (+0.4 microns of peak-to-valley defocus curvature added to the phase of the wavefront), in the plane of best focus, and in a plane following the plane of best focus (−0.4 microns of peak-to-valley defocus curvature added to the phase of the wavefront), respectively. Thus, these figures illustrate how it is possible to introduce a deformation of the wavefront emitted by the emitting particle that allows the axial symmetry of the PSF to be broken.

More generally, certain known algorithms allow the wavefront deformation required to obtain a desired PSF shape to be determined, such as, for example, the Gerchberg-Saxton algorithm. The article by G. Whyte et al. ("Experimental demonstration of holographic three dimensional light shaping using a Gerchberg-Saxton algorithm", New J. Phys. 7, 117 (2005)) describes an example application of this algorithm. However, these algorithms are quite complex and in general return solutions based on deformations of the phase of the wavefront comprising phase jumps, i.e. a discontinuous phase that can only be produced with a liquid-crystal phase modulator. One advantage of the use of polynomials or combinations of Zernike polynomials of even azimuthal order is that the latter allow wavefront deformations to be obtained with continuous and continuously derivable phases that can easily be produced with a deformable mirror having a continuous membrane.

Spatial modulation of the wavefront by way of the spatial modulator such as described above allows other functionalities to be delivered by the three-dimensional localization device according to one or more embodiments of the invention. For example, it is possible to achieve dynamic focusing by introducing a controlled defocus into the wavefront. There are a number of possible applications of dynamic focusing. For example, it allows an emitting particle to be tracked dynamically. To do this, a correction control signal allowing the emitting particle to be focused on in real time is transmitted to the wavefront modulator, which is, for example, a deformable mirror. This allows the particle to be tracked by measuring the modification of the focus applied, without having to move the sample, especially in order to track particles over wide operating ranges. More generally, dynamic focusing allows the region of interest of the sample to be moved without moving the sample itself. Dynamic focusing may be coupled with the choice of the controlled deformation introduced in order to determine the axial position of the emitting particle. For example, in a first step, a large astigmatism may be introduced, allowing the emitting particle to be located in a large $\Delta z$ range. It is then possible to introduce a controlled defocus in order to focus on a smaller region of interest in the sample, thereby allowing the astigmatism value required for the measurement to be reduced and the amount of photons per pixel to be increased, due to the smaller size of the PSF.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

The invention claimed is:

1. A super-resolution microscopy method for three-dimensional localization of a plurality of emitting particles, comprising:
   forming at least one image of each of said plurality of emitting particles in a detection plane of a detector by a microscopy imaging system;
   correcting, by a wavefront-modulating device, at least some of the optical defects present between said plurality of emitting particles and said detection plane; and introducing, via said wavefront-modulating device, a deformation of the wavefront emitted by each of said emitting particles, of controlled amplitude, allowing a bijective relationship to be formed between the shape of the image of each of said plurality of emitting panicles in the detection plane and the axial position of said emitting particle relative to an object plane that is optically conjugated with the detection plane by the microscopy imaging system, wherein the axial position of said emitting particle is within a given range of values of axial positions determined by the amplitude of said deformation; and determining the axial position of at least one of said plurality of emitting particles relative to the object plane based on the shape of the image of said at least one emitting particle.

2. The method as claimed in claim 1, comprising a prior step of analyzing said optical defects present between said plurality of emitting particles and said detection plane, by a wavefront analyzing device.

3. The method as claimed in claim 1, wherein the correction of all or some of the optical defects is carried out iteratively, on the basis of a measure of the quality of an image formed of at least one of said plurality of emitting particles.

4. The method as claimed in claim 1, furthermore comprising the emission of one or more light beams for exciting at least one emitting particle, allowing said particle to emit a light signal in a given range of wavelengths.

5. The method as claimed in claim 1, wherein the controlled deformation is an astigmatism.

6. The method as claimed in claim 1, furthermore comprising a step of focusing dynamically on at least one of said plurality of emitting particles, said dynamic focus being obtained by controllably defocusing the wavefront emitted by said emitting particle by the wavefront-modulating device.

7. A wavefront-controlling device intended to be connected to a super-resolution microscopy system for localizing a plurality of emitting particles, the microscopy system comprising a microscope equipped with an optical imaging system and a detector, the wavefront-controlling device comprising:

a relay optical system for optically conjugating an entrance plane and an exit plane that are intended to be coincident with an image plane of said optical imaging system of the microscope and a detection plane of the detector, respectively, when said wavefront-controlling device is connected to the super-resolution microscopy system;

a wavefront-modulating device, comprising a correction plane and allowing the wavefront emitted by each of said plurality of emitting particles to be modulated when said wavefront-controlling device is connected to the super-resolution microscopy system;

an optical system allowing an entrance pupil plane of the wavefront-controlling device to be optically conjugated with said correction plane, said pupil plane being intended to be coincident with the exit pupil of the optical imaging system of the microscope when said wavefront-controlling device is connected to the super-resolution microscopy system; and a controller for controlling said wavefront-modulating device allowing, when the wavefront-controlling device is connected to the super-resolution microscopy system, correction of at least some of the optical defects present between said plurality of emitting particles and said detection plane, introduction of a deformation of the wavefront of controlled amplitude, allowing a bijective relationship between the shape of the image of each of said plurality of emitting particles in the detection plane and the axial position of said emitting particle relative to an object plane, which is optically conjugated with the detection plane, wherein the axial position of said emitting particle is within a given range of values of axial positions determined by the amplitude of said deformation, and determination of the axial position of at least one of said plurality of emitting particles relative to the object plane based on the shape of the image of said at least one emitting particle.

8. The wavefront-controlling device as claimed in claim 7, wherein the wavefront-modulating device is a deformable mirror.

9. The wavefront-controlling device as claimed in claim 7, furthermore comprising a device for analyzing optical defects, which device is connected to said controller.

10. The wavefront-controlling device as claimed in claim 9, wherein said device for analyzing optical defects is a Shack-Hartmann analyzer.

11. The wavefront-controlling device as claimed in claim 7, further comprising mechanical interfaces for connecting the wavefront-controlling device to the super-resolution microscopy system.

12. A super-resolution microscopy device for three-dimensional localization of a plurality of emitting particles, comprising:

a system for imaging each of said plurality of emitting particles in a detection plane of a detector;

a wavefront-modulating device, allowing the wavefront emitted by each of said plurality of emitting particles to be modulated;

a controller for controlling said wavefront modulating device, allowing:

correction of at least some of the optical defects present between said plurality of emitting particles and said detection plane, introduction of a deformation of the wavefront of controlled amplitude, allowing a bijective relationship between the shape of the image of each of said plurality of emitting particles in the detection plane and the axial position of said emitting particle relative to an object plane, which is optically conjugated with the detection plane, wherein the axial position of said emitting particle is within a given range of values of axial positions determined by the amplitude of said deformation, and determination of the axial position of at least one of said plurality of emitting particles relative to the object plane based on the shape of the image of said at least one emitting particle.

13. The device for three-dimensional localization as claimed in claim 12, wherein the wavefront-modulating device includes a correction plane that is optically conjugated with the pupil of said imaging system.

14. The device for three-dimensional localization as claimed in claim 12, wherein the wavefront-modulating device is a deformable mirror.

15. The device for three-dimensional localization as claimed in claim 12, further comprising a device for analyzing optical defects, wherein the device is connected to said controller.

16. The device for three-dimensional localization as claimed in claim 15, wherein said device for analyzing optical defects is a Shack-Hartmann analyzer.

17. The device for three-dimensional localization as claimed in claim 12, wherein said controller ensures the correction of all or some of the optical defects iteratively, on the basis of a measure of the quality of the images formed of at least one of said plurality of emitting particles.

18. The device for three-dimensional localization as claimed in claim 12, furthermore comprising a device for emitting one or more light beams for exciting at least one emitting particle, allowing said particle to emit a light signal in a given range of wavelengths.

* * * * *